US009518289B2

United States Patent
Chun et al.

(10) Patent No.: US 9,518,289 B2
(45) Date of Patent: Dec. 13, 2016

(54) DETECTION OF TARGET NUCLEIC ACID SEQUENCES BY EXONUCLEOLYTIC ACTIVITY USING SINGLE-LABELED IMMOBILIZED PROBES ON SOLID PHASE

(75) Inventors: Jong Yoon Chun, Seoul (KR); Young Jo Lee, Seoul (KR)

(73) Assignee: Seegene, Inc., Seoul (KR)

( * ) Notice: Subject to any disclaimer, the term of this patent is extended or adjusted under 35 U.S.C. 154(b) by 0 days.

(21) Appl. No.: 13/824,688

(22) PCT Filed: Dec. 23, 2010

(86) PCT No.: PCT/KR2010/009268
§ 371 (c)(1),
(2), (4) Date: Mar. 18, 2013

(87) PCT Pub. No.: WO2012/039529
PCT Pub. Date: Mar. 29, 2012

(65) Prior Publication Data
US 2013/0190208 A1    Jul. 25, 2013

(30) Foreign Application Priority Data
Sep. 20, 2010    (KR) .................. 10-2010-0092554

(51) Int. Cl.
*C12Q 1/68*    (2006.01)
(52) U.S. Cl.
CPC .......... *C12Q 1/6834* (2013.01); *C12Q 1/6816* (2013.01); *C12Q 1/6823* (2013.01); *C12Q 1/6876* (2013.01)
(58) Field of Classification Search
None
See application file for complete search history.

(56) References Cited

U.S. PATENT DOCUMENTS 5,487,972 A * 1/1996 Gelfand et al. ............ 435/6.1
2003/0198979 A1 10/2003 Cho et al.
(Continued)

FOREIGN PATENT DOCUMENTS

| EP | 0360940 A2 | 4/1990 |
| EP | 1777298 A1 | 4/2007 |
| WO | WO 2008/011004 A2 | 1/2008 |

OTHER PUBLICATIONS

Liu et al (2006) "TaqMan probe array for quantitative detection of DNA targets" Nucleic Acids Research 34(1):e4.*
(Continued)

*Primary Examiner* — Tracy Vivlemore
*Assistant Examiner* — Karen S Weiler
(74) *Attorney, Agent, or Firm* — Clark & Elbing LLP; Susan M. Michaud

(57) ABSTRACT

The present invention relates to a novel method for detection of target nucleic acid sequences by cyclic exonucleolytic reactions (CER) or exonucleolytic reactions (ER) using single-labeled immobilized probes on a solid phase. The present invention enables to detect target nucleic acid sequences on a solid phase using single-labeled systems. Comparing with multiple-labeled systems such as dual labeling, the present invention using single-labeled probes has excellent advantages in light of convenience and cost effectiveness in probe design and preparation. Furthermore, the measurement of changes of the signal decrease during reactions is responsible for more accurate qualitative and quantitative analysis of target nucleic acid sequences.

17 Claims, 5 Drawing Sheets

Fluorescent signal decrease in the detection of a target nucleic acid

When a single-labeled probe is hybridized with a target nucleic acid sequence, the 5'-end portion of the probe is digested by an enzyme having a 5' to 3' exonuclease activity. The release of the label from the probe results in decrease in the signal on the solid substrate.

(R) : Reporter molecule

(56) References Cited

U.S. PATENT DOCUMENTS

2006/0292579 A1\* 12/2006 Lockhart et al. ................ 435/6
2009/0186349 A1\* 7/2009 Gunderson et al. ............. 435/6

OTHER PUBLICATIONS

Ahern (1995) "Biochemical, Reagents Kits Offer Scientists Good Return on Investment" The Scientist, 9(15):20.\*
International Search Report for PCT/KR2010/009268, mailed Nov. 22, 2011 (4 pages).

\* cited by examiner

Fluorescent signal decrease in the detection of a target nucleic acid

When a single-labeled probe is hybridized with a target nucleic acid sequence, the 5'-end portion of the probe is digested by an enzyme having a 5' to 3' exonuclease activity. The release of the label from the probe results in decrease in the signal on the solid substrate.

(R) : Reporter molecule

Fluorescent images depending on various cycle numbers during cyclic exonucleolytic reaction

Fig. 2B

Change of fluorescence intensity depending on various cycle numbers during cyclic exonucleolytic reaction

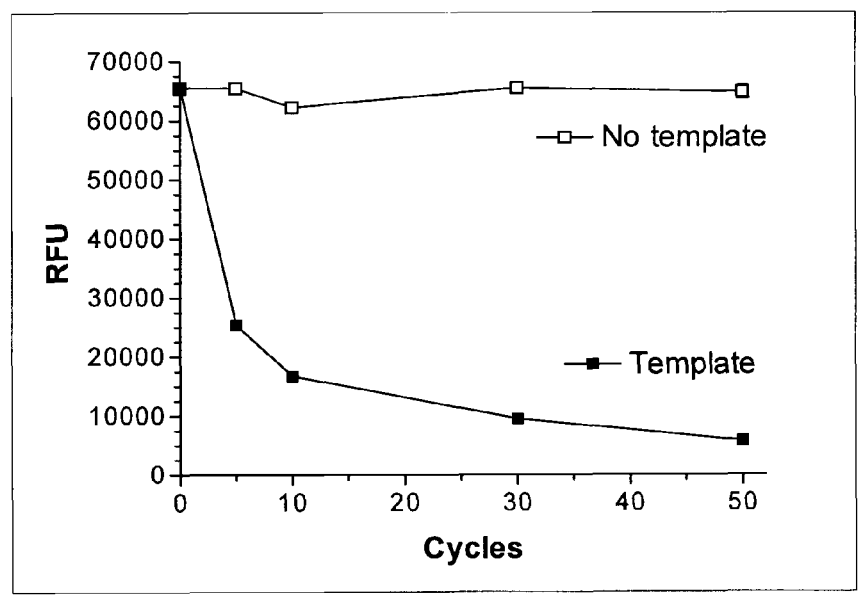

| Template[1] | Probe[2] | RFU[3] | | | | |
|---|---|---|---|---|---|---|
| | | No. of cycles : | 0 | 5 | 10 | 30 | 50 |
| - | SA_Con | | 65,471 (±0.00) | 65,462 (±0.00) | 62,226 (±9.90) | 65,454 (±0.00) | 64,699 (±1,071.97) |
| + | SA_Con | | 65,471 (±1.41) | 25,375 (±534.57) | 16,745 (±863.38) | 9,444 (±247.49) | 5,703 (±608.11) |

[1] Template is a synthetic oligonucleotide for *Staphylococcus aureus* gene.
[2] Probe has a fluorescent reporter molecule at its 5'-end.
[3] RFU represents relative fluorescence units and is measured at each cycle.

Fluorescent images depending on incubation time
during exonucleolytic reaction

Fig. 3B

Change of fluorescence intensity depending on incubation time during exonucleolytic reaction

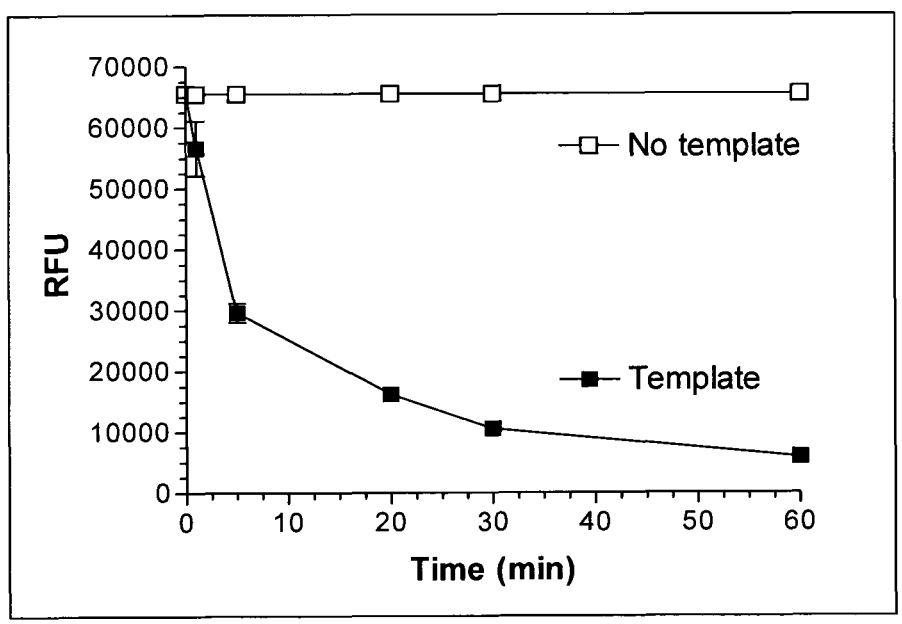

| Template[1] | Probe[2] | | RFU[3] | | | | | |
|---|---|---|---|---|---|---|---|---|
| | | Time[4] | 0 min | 1 min | 5 min | 20 min | 30 min | 60 min |
| - | SA_Con | | 65,464 (±0.7) | 65,433 (±1.4) | 65,444 (±1.4) | 65,443 (±1.4) | 65,426 (±1.4) | 65,449 (±0.7) |
| + | SA_Con | | 65,449 (±11.3) | 56,576 (±4,471.0) | 29,603 (±1,547.9) | 16,171 (±206.5) | 10,540 (±47.4) | 5,889 (±100.4) |

[1] Template is a synthetic oligonucleotide for *Staphylococcus aureus* gene.
[2] Probe has a fluorescent reporter molecule at its 5'-end.
[3] RFU represents relative fluorescence units and is measured at each time.
[4] Time represents an incubation time at 55 ℃.

SEQUENCE LISTING

<160> NUMBER OF SEQ ID NOS: 3

<210> SEQ ID NO 1
<211> LENGTH: 70
<212> TYPE: DNA
<213> ORGANISM: Artificial Sequence
<220> FEATURE:
<223> OTHER INFORMATION: synthetic template

<400> SEQUENCE: 1
ggtgtaggtg gtggcggtaa caacgccgta aaccgaatga ttgaccacgg aatgaataat    60
gttgaattta    70

<210> SEQ ID NO 2
<211> LENGTH: 44
<212> TYPE: DNA
<213> ORGANISM: Artificial Sequence
<220> FEATURE:
<223> OTHER INFORMATION: probe

<400> SEQUENCE: 2
cattccgtgg tcaatcattc ggtttacggc gttgttacct tttt    44

```
<210> SEQ ID NO 3
<211> LENGTH: 10
<212> TYPE: DNA
<213> ORGANISM: Artificial Sequence
<220> FEATURE:
<223> OTHER INFORMATION: marker probe

<400> SEQUENCE: 3
atatatatat                                                              10
```

DETECTION OF TARGET NUCLEIC ACID SEQUENCES BY EXONUCLEOLYTIC ACTIVITY USING SINGLE-LABELED IMMOBILIZED PROBES ON SOLID PHASE

CROSS-REFERENCE TO RELATED APPLICATIONS

This application is the U.S. national stage filing under 35 U.S.C.§371 of International Application No. PCT/KR2010/009268, filed Dec. 23, 2010, which claims priority from Korean Patent Application 10-2010-0092554, filed Sep. 20, 2010.

BACKGROUND OF THE INVENTION

Field of the Invention

The present invention relates to a novel method for detection of target nucleic acid sequences by cyclic exonucleolytic reactions (CER) or exonucleolytic reactions (ER) using single-labeled immobilized probes on a solid phase.

Description of the Related Art

Microarray-based technologies are highlighted as promising tools for analyzing the presence, level or expression patterns of a gene or a gene population (Schena et al., 1995. Quantitative Monitoring of Gene Expression Patterns with a Complementary DNA Microarray, *Science,* 270:467-470; DeRisi et al., 1996, Use of a cDNA Microarray to Analyse Gene Expression Patterns in Human Cancer, *Nature Genetics* 14:457-460). However, since the conventional DNA microarray methods depend mostly on hybridization to detect target nucleotide sequences, they have serious shortcomings of a high rate of false positives. In particular, cross reactions (non-specific hybridizations) usually occurring in the conventional DNA microarrays and decreased sensitivity give rise to a sharp decrease in reliability of final hybridization signals (William E. Bunney, et al. 2003. Microarray Technology: A Review of New Strategies to Discover Candidate Vulnerability Genes in Psychiatric Disorders, *Am. J. Psychiatry* 160:4, 657-666).

To overcome such problems of microarray-based technologies, a variety of novel microarray approaches have been suggested depending on not only hybridization but also enzymatic reactions such as DNA polymerase reactions or ligase reactions for elevating reliability of target detection.

The single base extension (SBE) or minisequencing method (SBE: Shumaker et al. Mutation detection by solid phase primer extension. Hum. Mutat. 7:346-354 (1996); Pastinen, et al., Minisequencing: a specific tool for DNA analysis and diagnostics on oligonucleotide arrays. Genome Res. 7:606-614 (1997)) employs 5' to 3' DNA polymerases in the presence of single-labeled ddNTPs to induce a single base extension of primers with single-labeled ddNTPs for target detection.

The ligation method (Affymetrix, INC, Enzymatic methods for genotyping on arrays, U.S. Pub. No. US2008/0131894) detects target sequences by ligation between array probes and single-labeled probes using ligases.

Although these conventional methods provide microarray-based target detection approaches using a single label molecule, these methods have serious shortcomings. For example, the SBE method and the ligation method require additional components, labeled ddNTPs and second labeled probes, respectively, and require additional reactions for these additional components. In addition, these methods are very likely to generate false positive signals due to inherent reaction error rates associated with DNA polymerases and ligases.

In the meantime, a solid phase-based TaqMan probe method has been reported to detect target sequences using 5' to 3' nuclease activities of DNA polymerases and dual-labeled probes (Liu et al., TaqMan probe array for quantitative detection of DNA targets, Nucleic Acid Res. 34:e4 (2006)). In the method, the dual-labeled probes are immobilized on a solid substrate. The method detects target sequences by measuring increase in signals from cleavage of dual-labeled probes by primer-dependent 5' to 3' nuclease activities of DNA polymerases. The primer-dependent 5' to 3' nuclease activities means that the dual-labeled probes are cleaved only by DNA polymerases bound to upstream primers or extended products of upstream primers.

This dual-labeled method possesses quite troublesome consideration factors. For example, the positions of reporter and quencher molecules on probes have to be determined by considering separation of two label molecules by enzymatic cleavage and remaining of reporter molecules on solid substrates even after the cleavage reactions. Upon increasing the distance between reporter and quencher molecules, the background signals are more likely to be generated because of unstable quenching. These tricky considerations associated with dual-labeled systems on probes are responsible for limitations and difficulties in probe design for the solid phase-based TaqMan probe method. Furthermore, the utilization of two label molecules is unfavorable in view of cost-effectiveness. In addition to this, the requirement for additional upstream primers for cleavage reactions makes this method to be worse.

Therefore, there remain long-felt needs in the art to develop novel DNA microarray technologies for detecting a target sequence, preferably a multiple of target sequences on a microarray by using only a single label molecule in a more convenient, reliable and reproducible manner. Furthermore, a novel real-time microarray method using only a single label molecule is also needed in the art for quantitative analysis of target nucleic acid sequences.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

Under such circumstances, the present inventor has made intensive studies to develop novel target detection technologies for detection, identification and quantitation of target nucleic acid sequences on a solid phase with no false positive and negative results in more convenient manner. As a result, the present inventors have established novel detection protocols on a solid phase in which signal decreases indicative of target nucleic acid sequences are generated and amplified on a solid phase by a cyclic exonucleolytic reaction (CER) or an exonucleolytic reaction (ER) using an immobilized probe having a single label. The novel detection protocols are very suitable in the detection of target nucleic acid sequences on a solid phase using a single label system.

Accordingly, it is an object of this invention to provide a method for detecting a target nucleic acid sequence from a DNA or a mixture of nucleic acids by a cyclic exonucleolytic reaction (CER) on a solid phase.

It is another object of this invention to provide a method for detecting a target nucleic acid sequence from a DNA or a mixture of nucleic acids by an exonucleolytic reaction (ER) on a solid phase.

It is still another object of this invention to provide a kit for detecting a target nucleic acid sequence from a DNA or a mixture of nucleic acids by a cyclic exonucleolytic reaction (CER) or an exonucleolytic reaction (ER) on a solid phase.

Other objects and advantages of the present invention will become apparent from the detailed description to follow taken in conjugation with the appended claims and drawings.

BRIEF DESCRIPTION OF THE DRAWINGS

FIGS. 2A and 2B represent the results of target detection by cyclic exonucleolytic reactions (CER) of the present invention using single-labeled probes immobilized on a solid substrate. FIG. 2A shows the fluorescent images corresponding to the cycle numbers, and FIG. 2B shows the fluorescent intensities of the images.

FIGS. 3A and 3B represent the results of target detection by exonucleolytic reactions (ER) of the present invention using single-labeled probes immobilized on a solid substrate. FIG. 3A shows the fluorescent images corresponding to the incubation time, and FIG. 3B shows the fluorescent intensities of the images.

DETAILED DESCRIPTION OF THIS INVENTION

Figure 1:
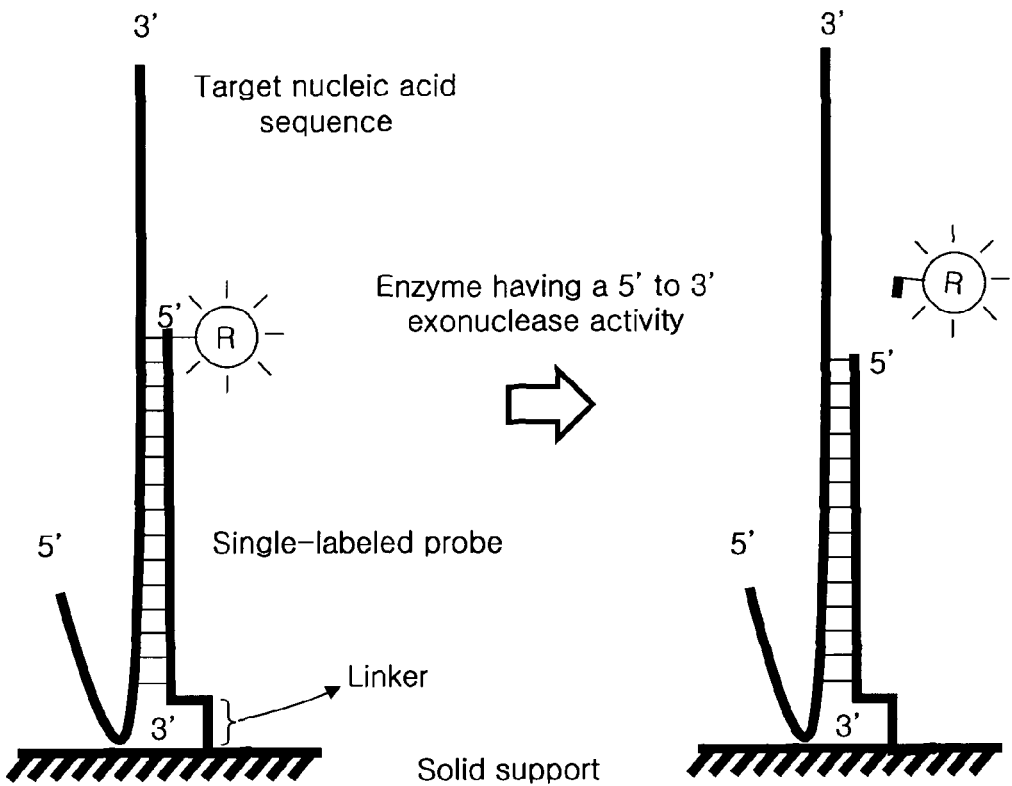
FIG. 1 schematically represents the process of the present invention. When a single-labeled immobilized probe on a solid substrate is hybridized with a target nucleic acid sequence, its 5'-end portion is digested by enzymes having a 5' to 3' exonuclease activity to release a single label from the probe. The release of the single label is responsible for decrease in a signal on the solid substrate, indicating the presence of the target nucleic acid sequence.

The present invention is drawn to novel solid-phase methods using single-labeled probes and 5' to 3' exonuclease.

The present invention is carried out by cyclic exonucleolytic reactions (CER) or non-cyclic exonucleolytic reactions [hereinafter referred to as exonucleolytic reactions (ER)] on solid substrates.

The present inventor has made intensive studies to develop novel target detection technologies for detection, identification and quantitation of target nucleic acid sequences on a solid phase with no false positive and negative results in more convenient manner. As a result, the present inventors have established novel detection protocols on a solid phase in which signal decreases indicative of target nucleic acid sequences are generated and amplified on a solid phase by a cyclic exonucleolytic reaction (CER) or an exonucleolytic reaction (ER) using an immobilized probe having a single label. The novel detection protocols are very suitable in the detection of target nucleic acid sequences on a solid phase using a single label system.

The term used herein "cyclic exonucleolytic reaction" refers to cleavage reactions by 5' to 3' exonuclease activities with cycles of hybridization and denaturation.

The term used herein "exonucleolytic reaction" refers to 5' to 3' exonuclease activity-induced cleavage reactions in which a single-labeled probe is hybridized with and released from a target nucleic acid sequence with no help of an artificial (intentional) denaturation step and a new single-labeled probe is then hybridized with the target nucleic acid sequence.

The term used herein "signal decrease" means the decrease in signals detected on a solid substrate on which single-labeled probes are immobilized. The present invention detects the signal decrease rather than signal increase for detecting target nucleic acid sequences. The term used herein "amplification of signal decrease" means that signals detected on a solid substrate are more decreased. According to the present invention, the signal decrease is amplified to detect target nucleic acid sequences in more accurate and sensitive manner.

The present inventors have conceived that T7 exonuclease or some DNA polymerases catalyzing the sequential removal of 5' nucleotides from duplex DNA in the 5' to 3' direction may induce the signal change from single-labeled probes immobilized on a solid phase upon hybridizing with target nucleic acid sequences.

Upon hybridizing with target nucleic acid sequences, single-labeled probes immobilized on a solid phase form double strand nucleic acid molecules to be specifically recognized by the enzyme having 5' to 3' exonuclease activity for cleavage reaction. The single label present on the 5'-end portion of the probes is released by the cleavage reaction and the signal decrease is induced on the solid phase, allowing for detecting the presence of target nucleic acid sequences. In addition, the present inventor has discovered that the amplification of signal decrease on the solid phase could be accomplished by cyclic exonucleolytic reactions or exonucleolytic reactions with no help of amplification of target nucleic acid sequences, enabling to detect target nucleic acid sequences on the solid phase in much more accurate and sensitive manner.

The conventional technologies for target detection in solid phase were most focused on detecting signals at the end of reactions.

Unlikely, on the basis that signal intensities are changed during the amplification of signal decrease by cyclic exonucleolytic reactions or exonucleolytic reactions, the present inventor has detected changes of signal decrease, which allows for more accurate qualitative and quantitative analysis of target nucleic acid sequences.

Signals on a solid substrate can be detected or measured using suitable devices such as confocal laser scanners with no washing steps and with no interference of label molecules released from single-labeled probes immobilized on a solid substrate. Therefore, in the present invention, single-labeled probes immobilized on a solid substrate are cleaved upon hybridization with target nucleic acid sequences to release labels and the decrease in signal on a solid substrate can be detected in a real-time manner, thereby detecting target nucleic acid sequences in a real-time manner.

This invention exhibits higher target specificity due to the adapted enzymatic reactions and plausible advantages in light of elimination of background signals and cost-effectiveness owing to utilization of single label rather than dual label.

One of the features of the present invention is to detect target nucleic acid sequences by measuring a signal decrease on a solid substrate dependent on release of a single label molecule from probes. The conventional methods typically measure or analyze a signal generation (i.e., signal increase) on a solid substrate for determining the presence of target nucleic acid sequences. Therefore, the conventional methods require dual label systems or the help of additional labeled components (e.g., a labeled ddNTP or an additional labeled probe) in a single label system.

Interestingly, the present invention using single-labeled probes immobilized on a solid phase shows effects which are non-obtainable by single-labeled probes in a liquid phase.

Liquid phase-based target detection methods using single-labeled probes and 5' to 3' exonuclease will require complicated processes such as electrophoresis for determining cleavage of single-labeled probes. Unlikely, the present invention performed on a solid phase ensures that the occurrence of cleavage of probes is detected using even a single label with no help of complicated isolation steps.

The conventional liquid phase-based methods may not detect cleavage of single-labeled probes in a real-time manner. In contrast, the present invention performed on a solid phase permits to detect cleavage of single-labeled probes in a real-time manner.

I. Target Detection by CER Using Single-Labeled Probes on Solid Substrate

In one aspect of this invention, there is provided a method for detecting a target nucleic acid sequence from a DNA or a mixture of nucleic acids by a cyclic exonucleolytic reaction (CER) on a solid phase, which comprises the steps of:

(a) hybridizing the target nucleic acid sequence with an immobilized probe having a nucleotide sequence complementary to the target nucleic acid sequence and having a single label generating a detectable signal; wherein the immobilized probe is immobilized on a solid substrate through its 3'-end;

(b) contacting the resultant of step (a) to a thermostable enzyme having a 5' to 3' exonuclease activity under conditions for cleavage of the immobilized probe; wherein the immobilized probe is digested by the thermostable enzyme having the 5' to 3' exonuclease activity to release the single label from the immobilized probe, resulting in decrease in a signal on the solid substrate;

(c) denaturing the resultant of step (b);

(d) repeating the steps (a)-(c) at least twice to further decrease the signal on the solid substrate; and (e) detecting the signal decrease on the solid substrate, such that the signal decrease by the cleavage of the immobilized probe is indicative of the presence of the target nucleic acid sequence.

The present invention by cyclic exonuleolytic reactions (CER) is drawn to a novel approach to obtain signals on a solid phase for the detection of target nucleic acid sequences by cyclic exonuleolytic reactions (CER) comprising (i) signal decrease by the cleavage of single labeled probes by thermostable enzymes having the 5' to 3' exonuclease activity and (ii) signal amplification (i.e. amplifying the signal decrease) by repetition of hybridization and denaturation between single labeled probes and the target nucleic acid sequence.

The CER process of the present invention permits amplification of the signal decrease by cycles of hybridization and denaturation. The CER process ensures amplification of the signal decrease indicative of the presence of target nucleic acid sequences with no amplification of target nucleic acid sequences, allowing for detection of target nucleic acid sequences in minute amounts. In addition, the CER process amplifies the signal decrease in more rapid and effective manner within a relative short time of the cleavage reaction. The repetition of hybridization and artificial (intentional) denaturation steps increases opportunities for hybridization between a target nucleic acid sequence and an uncleaved single-labeled probe, resulting in amplification of the signal decrease. Furthermore, a repeated hybridization in a relative short time reduces possibilities of non-specific hybridization, contributing to preventing non-specific signals. Where a double stranded target nucleic acid sequence is used, it is denatured into a single strand at each cycle and then involved in hybridization. In this regard, the CER process exhibits more effective hybridization reactions than the ER process with no artificial (intentional) denaturation step.

In the present invention, the target nucleic acid sequence is hybridized with the single-labeled probe immobilized on the solid substrate.

The term used herein "target nucleic acid", "target nucleic acid sequence" or "target sequence" refers to a nucleic acid sequence of interest for detection, which is annealed to or hybridized with a probe or a primer under hybridization, annealing or amplifying conditions.

The term used herein "probe" refers to a single-stranded nucleic acid molecule comprising a portion or portions that are substantially complementary to a target nucleic acid sequence. Preferably, the probe is a single-stranded deoxyribonucleotide molecule. The probes may also include ribonucleotides.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. The primer is preferably single stranded for maximum efficiency in amplification. Preferably, the primer is an oligodeoxyribonucleotide.

The probes and primers used in this invention may be comprised of naturally occurring dNMP (i.e., dAMP, dGM, dCMP and dTMP), modified nucleotide, or non-natural nucleotide.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

There is no intended distinction between the terms "annealing" and "hybridizing", and these terms will be used interchangeably.

The immobilized probes used in this invention have a nucleotide sequence complementary to target nucleic acid sequences. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary.

The immobilized probes used in this invention are immobilized via its 3'-end on the solid substrate. A preferable solid substrate includes suitable solid or semi-solid supporters, such as membrane, filter, chip, slide, wafer, fiber, magnetic or nonmagnetic bead, gel, tubing, plate, macromolecule, microparticle and capillary tube.

In many embodiments, at least one surface of the solid substrate will be substantially flat, although in some embodiments it may be desirable to physically separate synthesis regions for different compounds with, for example, wells, raised regions, pins, etched trenches, or the like. According to other embodiments, the solid substrate(s) will take the form of beads, resins, gels, microspheres, or other geometric configurations.

Preferably, the solid substrate comprises a microarray. The probes may be immobilized directly or indirectly (preferably indirectly) onto the surface of the solid substrate. Furthermore, the probes may be immobilized on the surface of the solid substrate in a covalent or non-covalent manner. Where the probes are immobilized indirectly onto the surface of the solid substrate, suitable linkers may be used. The linkers useful in this invention may include any linkers utilized for probe immobilization on a microarray. For example, alkyl or aryl compounds with amine functionality, or alkyl or aryl compounds with thiol functionality serve as linkers for probe immobilization. In addition, a poly (T) tail or a poly (A) tail may be used as linkers for increasing hybridization efficiency and decreasing space hindrance which is very likely to inhibit enzymatic actions (e.g., enzymatic cleavage reactions). The poly (T) tail or a poly (A) tail is considered not to be contained in sequences of probes.

The microarray to provide a reaction environment in this invention may include any those known to one of skill in the art. All processes of the present invention, i.e., annealing to target nucleic acid, extension/digestion and fluorescence detection, are carried out on the microarray. The immobilized probes on the microarray serve as hybridizable array elements. The solid substrate to fabricate microarray include, but not limited to, metals (e.g., gold, alloy of gold and copper, aluminum), metal oxide, glass, ceramic, quartz, silicon, semiconductor, $Si/SiO_2$ wafer, germanium, gallium arsenide, carbon, carbon nanotube, polymers (e.g., polystyrene, polyethylene, polypropylene and polyacrylamide), sepharose, agarose and colloids. A plurality of immobilized probes in this invention may be immobilized on an addressable region or two or more addressable regions on a solid substrate that may comprise 2-1,000,000 addressable regions. Immobilized probes may be fabricated to produce array or arrays for a given application by conventional fabrication technologies such as photolithography, ink-jetting, mechanical microspotting, and derivatives thereof.

Since the immobilized probes on the solid substrate are physically separated from one another, a multiple of target nucleic acid sequences can be detected on the solid substrate even when a single type of a label molecule is used.

The immobilized probes used in this invention have a single label generating a detectable signal. The single label comprises, but not limited to, a chemical label (e.g., biotin), an enzymatic label (e.g., alkaline phosphatase, β-galactosidase, β-glucosidase, luciferase, cytochrome $P_{450}$ and horseradish peroxidase), a radioactive label (e.g., $C^{14}$, $I^{125}$, $P^{32}$ and $S^{35}$), a fluorescent label, a luminescent label, a chemiluminescent label or a metal label (e.g., gold).

According to a preferred embodiment, the single label is a label capable of generating signals in a real-time manner. More preferably, the single label is a fluorescent label.

The preferable examples of fluorescent labels are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC(5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer.

Suitable fluorescent labels are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition, Molecular Probes, Eugene, Oreg., 1996; U.S. Pat. Nos. 3,996,345 and 4,351,760.

The single label molecule may be linked to probes in accordance with various methods. Preferably, the single label molecule is linked to probes via spacers containing at least three carbon atoms (e.g., 3-carbon spacer, 6-carbon spacer, 9-carbon spacer or 12-carbon spacer).

According to a preferred embodiment, the single label on the immobilized probe is located at its 5'-end or at 1-5 nucleotides apart from its 5'-end, more preferably at its 5'-end or at 1-4 nucleotides apart from its 5'-end, still more preferably at its 5'-end or at 1-3 nucleotides apart from its 5'-end, still further more preferably at its 5'-end or at 1-2 nucleotides apart from its 5'-end, most preferably at its 5'-end.

The annealing or hybridization of probes or primers may be a wide variety of hybridization processes known to those of skill in the art. The suitable hybridization conditions in the present invention may be routinely determined by optimization procedures. Conditions such as temperature, concentration of components, hybridization and washing time, buffer components, and their pH and ionic strength may be varied depending on various factors, including the length and GC content of oligonucleotides such as probes and target nucleic acid sequences. The detailed conditions for hybridization can be found in Joseph Sambrook, et al., *Molecular Cloning, A Laboratory Manual*, Cold Spring Harbor Laboratory Press, Cold Spring Harbor, N.Y. (2001);

and M. L. M. Anderson, *Nucleic Acid Hybridization*, Springer-Verlag New York Inc. N.Y. (1999).

For example, the hybridization temperature of the immobilized probe with target nucleic acid sequences ranges from about 30° C. to 80° C., more preferably 40° C. to 75° C., still more preferably 50° C. to 72° C.

Following the hybridization reaction, the resultant of step (a) is contacted to a thermostable enzyme having a 5' to 3' exonuclease activity under conditions for cleavage of the immobilized probe. The single label is released from the immobilized probe by the thermostable enzyme having the 5' to 3' exonuclease activity, only when the immobilized probe is hybridized with the target nucleic acid sequence, finally inducing decrease in a signal on the solid substrate (see FIG. 1). The signal decrease by the cleavage of the immobilized probe is indicative of the presence of the target nucleic acid sequence.

The phrase "conditions for cleavage of the immobilized probe" means the reaction conditions for digestion of the immobilized probe by enzymes having the 5' to 3' exonuclease activity, including temperature, pH, ionic strength, buffer, probe length and sequence, and types of exonucleases.

According to the preferred embodiment, hybridization and cleavage reaction is conducted for no more than 10 min, preferably no more than 5 min, more preferably no more than 1 min, still more preferably no more than 0.5 min. According to the preferred embodiment, the hybridization and cleavage reaction is conducted for at least 5 sec, preferably at least 10 sec, more preferably at least 20 sec.

The thermostable enzymes having the 5' to 3' exonuclease activity include heat-stable enzymes that catalyze an exonucleolytic reaction in a 5' to 3' direction by acting on probes involved in hybridization with target nucleic acid sequences. The enzymes do not digest single-stranded nucleic acid molecules.

Alternatively, the single-labeled probe used in this invention further comprises at least one mismatch nucleotide at its 5'-end. Some 5' to 3' exonucleases exhibit not only exonuclease activity but also 5' to 3' endonuclease activity depending on conditions (see Murante et al., Journal of Biological Chemistry, 269:1191-1196 (1994)). Therefore, where the single-labeled probe with at least one mismatch nucleotide at its 5'-end is employed, the present invention may detect the target nucleic acid sequence dependent on type of 5' to 3' exonucleases (e.g., Taq DNA polymerase) and reaction conditions. Preferably, the single-labeled probe further comprises 1-3 mismatch nucleotides at its 5'-end. Preferably, the single label molecule is located at the mismatch nucleotide.

Preferably, the thermostable enzyme having the 5' to 3' exonuclease activity is a thermostable template-dependent nucleic acid polymerase having the 5' to 3' exonuclease activity, more preferably a thermostable DNA polymerase obtained from a variety of bacterial species, including *Thermus aquaticus* (Taq), *Thermus thermophilus, Thermus filiformis, Thermus flavus, Thermus antranikianii, Thermus caldophilus, Thermus chliarophilus, Thermus igniterrae, Thermus lacteus, Thermus oshimai, Thermus ruber, Thermus rubens, Thermus scotoductus, Thermus silvanus, Thermus* species Z05 and *Thermus* species sps 17. Most preferably, the template-dependent nucleic acid polymerase having the 5' to 3' exonuclease activity is Taq DNA polymerase.

The immobilized probe hybridized with the target nucleic acid sequence is digested by the thermostable enzyme having the 5' to 3' exonuclease activity to release the single label from the immobilized probe, thereby decreasing a signal on the solid substrate.

After the cleavage reaction of the immobilized probe, the resultant of step (b) is denatured. Methods for denaturation include, but not limited to, heating, alkali, formamide, urea and glycoxal treatment, enzymatic methods (e.g., helicase action) and binding proteins. For instance, the denaturation may be achieved by heating at temperature ranging from 70° C. to 105° C. General methods for accomplishing this treatment are provided by Joseph Sambrook, et al., Molecular Cloning, A Laboratory Manual, Cold Spring Harbor Laboratory Press, Cold Spring Harbor, N.Y. (2001).

Preferably, the denaturation in this invention is carried out under conditions that hybridization between the target nucleic acid sequence and the probe does not occur. Where a double-stranded target nucleic acid sequence is employed, it is preferable that the denaturation is performed under conditions that the target nucleic acid sequence is denatured into a single strand.

Afterwards, the steps (a)-(c) are repeated at least twice (preferably at least five times, more preferably at least ten times) to further decrease the signal on the solid substrate.

The repetition of hybridization, cleavage and denaturation (i.e., cyclic exonucleolytic reactions) amplifies signal decrease and is responsible for the signal change on the solid substrate.

The reaction conditions including concentrations and sequences of nucleic acid molecules (target nucleic acid sequences and probes), and the type and activity of enzymes used influence on the extent of signal decrease. The measurement of signal decrease patterns provides a variety of useful information (e.g., qualitative and quantitative analysis of target nucleic acid sequences).

In the present invention, the signal decrease may be detected at the end of the cyclic reactions or during the cyclic reactions, giving rise to more accurate qualitative and quantitative analysis of target nucleic acid sequences.

In this regard, the cyclic exonucleolytic reaction using single-labeled probes on the solid substrate is very useful in a quantitative detection of target nucleic acid sequences.

Finally, the signal decrease on the solid substrate is detected, such that the signal decrease by the cleavage of the immobilized probe is indicative of the presence of the target nucleic acid sequence.

The signal detection may be performed at the end of the repetition (i.e., end-point manner), for each cycle of the repetition real-time manner), or at each of predetermined time intervals during the repetition. Preferably, the signal detection may be performed for each cycle of the repetition or at each of predetermined time intervals during the repetition.

The signal may be detected or measured by conventional methods for each label. For example, the fluorescence signal may be detected or measured by conventional methods, e.g., fluorometers.

A washing step may be carried out prior to the step (e). However, the present invention can detect only signals present on the solid substrate using suitable devices such as confocal laser scanners without washing the solid substrate and with no interference with label molecules released from the single-labeled probes on the solid substrate.

Therefore, the signal decrease may be detected in a real-time manner, which results in real-time detection of target nucleic acid sequences on the solid substrate in a more convenient and accurate manner.

According to a preferred embodiment, the step (a) further comprises a reverse primer to produce the target nucleic acid sequence hybridizable with the immobilized probe. Where the reverse primer are used with the thermostable DNA polymerase having the 5' to 3' exonuclease activity, a template to be hybridized with the probe is selectively increased by nucleic acid synthesis reactions during the repetition step. The increase in the template allows for more rapidly providing signals to detect target sequences.

Alternatively, the step (a) further comprises an upstream primer or probe to be hybridized with a site downstream of a hybridized site of the immobilized probe.

The term used herein "upstream primer" refers to a primer to be hybridized with a site downstream of a hybridized site of the immobilized probe and to form a complementary sequence to the target nucleic acid sequence, such that the primer is extendible with help of the template-dependent nucleic acid polymerase. The term used herein "upstream probe" refers to a non-extendible probe to be hybridized with a site downstream of a hybridized site of the immobilized probe. Either upstream primer or upstream probe is positioned upstream of the 5'-end of the immobilized probe.

The template-dependent nucleic acid polymerase having the 5' to 3' exonuclease activity extends the upstream primer and then digests the immobilized probe. Alternatively, upon contacting to the upstream probe (or upstream primer) present adjacent to the immobilized probe, the enzyme may also digest the immobilized probe. Where the upstream primer or probe is used, the immobilized probe may be digested by an upstream primer or probe-dependent 5' to 3' exonuclease activity of the template-dependent nucleic acid polymerase.

Where the 5' to 3' exonuclease activity of the template-dependent nucleic acid polymerase acts on a duplex of the target nucleic acid sequence and the single-labeled probe before the upstream primer or probe is hybridized with the target nucleic acid sequence, the present invention independent on the presence of the upstream primer or probe may induce the signal decrease. Therefore, where the upstream oligonucleotide (upstream primer or probe) is involved in the reaction, the signal decrease may be caused by not only oligonucleotide-dependent 5' to 3' exonuclease activities but also oligonucleotide-independent 5' to 3' exonuclease activities of DNA polymerases.

According to a preferred embodiment, the upstream probe and the immobilized probe are adjacently positioned to the extent that the template-dependent nucleic acid polymerase contacts simultaneously to both the 3'-end portion of the upstream probe and the 5'-end of the immobilized probe. Preferably, the 3'-end of the upstream probe is located at 1-20 nucleotides (more preferably 1-10 nucleotides, still more preferably 1-5 nucleotides) apart from the 5'-end of the immobilized probe. Most preferably, the 3'-end of the upstream probe is immediately adjacent to the 5'-end of the immobilized probe.

In the present invention, where both the upstream primer and the reverse primer are used, the target nucleic acid sequence can be detected simultaneously with amplification.

Preferably, the 3'-end of the upstream probe is blocked for prohibiting extension reactions. The non-extendable blocking for the upstream probe may be achieved by adding a non-complementary nucleotide or a chemical moiety such as a phosphate group to the 3'-hydroxyl group of the last nucleotide. In addition, the blocking may be performed by removing the 3'-hydroxyl group of the last nucleotide or introducing a nucleotide without the 3'-hydroxyl group such as dideoxynucleotide.

According to a preferred embodiment, the immobilized probe has a blocker site. The blocker site comprises a blocker at least one nucleotide resistant to cleavage by enzymes having a 5' to 3' exonuclease activity. The blocker site is positioned at a site to be cleaved by the enzyme having the 5' to 3' exonuclease activity when the immobilized probe is hybridized with the non-target nucleic acid sequence.

According to a preferred embodiment, the blocker site comprises 1-15 blockers, more preferably 2-10 blockers, still more preferably 3-8 blockers, still further more preferably 3-6 blockers. The blocker nucleotide present in the immobilized probe may be one or more in continuous or intermittent manner.

Nucleotides serving as blockers, i.e., those having a backbone resistant to cleavage by an enzyme having a 5' to 3' exonuclease activity include any one known to one of skill in the art. For example, they include various phosphorothioate linkages, phosphonate linkages, phosphoroamidate linkages and 2'-carbohydrates modifications. According to a preferred embodiment, nucleotides having a backbone resistant to cleavage by an enzyme having a 5' to 3' exonuclease activity include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, a-anomeric oligodeoxynucleotide and 1-(4'-thio-β-D-ribofuranosyl) modification. The blocker nucleotide present in the immobilized probe may be one or more in continuous or intermittent manner.

According to a preferred embodiment, the upstream and/or reverse primer additionally used for the present method have a dual priming oligonucleotide (DPO) structure represented by the following general formula I:

$$5'\text{-}X_p\text{—}Y_q\text{—}Z_r\text{-}3' \quad (I)$$

wherein, Xp represents a 5'-first priming portion having a hybridizing nucleotide sequence complementary to the target nucleic acid; Yq represents a separation portion comprising at least three universal bases, Zr represents a 3'-second priming portion having a hybridizing nucleotide sequence complementary to the target nucleic acid; p, q and r represent the number of nucleotides, and X, Y, and Z are deoxyribonucleotides or ribonucleotides; the $T_m$ of the 5'-first priming portion is higher than that of the 3'-second priming portion and the separation portion has the lowest $T_m$ in the three portions; the separation portion separates the 5'-first priming portion from the 3'-second priming portion in terms of annealing events to the target nucleic acid, whereby the annealing specificity of the oligonucleotide are determined dually by the 5'-first priming portion and the 3'-second priming portion such that the overall annealing specificity of the primer is enhanced.

Where the present invention is carried out using a primer, it is likely that conventional primers give rise to less specific detection of target nucleic acid sequences. Therefore, it is preferable to use primers having the DPO structure. However, the primer having the DPO structure elevates the target specificity of the present invention (see WO2006/095981).

The term "conventional" in conjunction with primers means any primer not having the DPO structure. They are described herein as conventional primers.

In the present invention, any probe may be used as immobilized probes having a single label molecule. Alternatively, the immobilized probe used in the present invention does not include a target discriminative probe (TD probe) having a modified dual specificity oligonucleotide (mDSO) structure. The mDSO structure is a newly modified version of a DSO (dual specificity oligonucleotide) structure that was first proposed by the present inventor (see WO 2006/095981). The DSO structure is also called DPO (dual priming oligonucleotide) as it serves as primers (Chun et al., Dual priming oligonucleotide system for the multiplex detection of respiratory viruses and SNP genotyping of CYP2C19 gene, *Nucleic Acid Research*, 35:6e40(2007)).

According to a preferred embodiment, the present invention is used for a quantitative detection of the target nucleic acid sequence. In particular, where the step (e) for detection is performed for each cycle of the repetition of step (d) or at each of predetermined time intervals during the repetition, the present invention is very useful in quantitative detection of the target nucleic acid sequence. The quantitative detection in the present invention may be accomplished with some modifications of conventional quantitative PCR methods (Sambrook, J. et al., *Molecular Cloning. A Laboratory Manual*, 3rd ed. Cold Spring Harbor Press (2001)). For example, the cyclic exonucleolytic reaction of the present invention and a standard curve are generally combined where the standard curve can associate the number of the target nucleic acid sequence which existed at the beginning of the reaction with the signal indicating the extent of the cleavage of probes. The standard curve can be generated by using a standard molecule of which number is known.

According to a preferred embodiment, the target nucleic acid sequence used in the present invention is a pre-amplified nucleic acid sequence obtained using an amplification primer.

The pre-amplified nucleic acid sequence may be obtained by various target amplification methods including Polymerase Chain Reaction (PCR), Ligase Chain Reaction (LCR), Strand Displacement Amplification (SDA), Transcription Mediated Amplification (TMA), Rolling Circle Amplification (RCA) or Nucleic Acid Sequence Bases Amplification (NASBA)

Preferably, the amplification primer has the DPO structure as described hereinabove.

The advantages of the present invention may be highlighted in the simultaneous (multiplex) detection of at least two target nucleic acid sequences.

According to a preferred embodiment, the target nucleic acid sequence comprises at least two types (more preferably, at least three types, still more preferably at least five types) of nucleic acid sequences and the immobilized probe comprises at least two types (more preferably, at least three types, still more preferably at least five types) of probes.

According to a preferred embodiment, the target nucleic acid sequence comprises at least two types (more preferably, at least three types, still more preferably at least five types) of nucleic acid sequences, the immobilized probe comprises at least two types (more preferably, at least three types, still more preferably at least five types) of probes, and the upstream primer and/or reverse primer comprises at least two types (more preferably, at least three types, still more preferably at least five types) of primers.

According to a preferred embodiment, the target nucleic acid sequence comprises at least two types (more preferably, at least three types, still more preferably at least five types) of nucleic acid sequences, the immobilized probe comprises at least two types (more preferably, at least three types, still more preferably at least five types) of probes, and the upstream probe comprises at least two types (more preferably, at least three types, still more preferably at least five types) of probes.

The target nucleic acid sequences to be detected by the present invention include, but not limited to, DNA (gDNA or cDNA) and RNA molecules. In addition, the present invention does not require any particular sequence or length of the target nucleic acid sequences to be detected and/or amplified. Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988)). For reverse transcription, a random hexamer or an oligonucleotide dT primer hybridizable to mRNA can be used. The oligonucleotide dT primer is comprised of dTMPs, one or more of which may be replaced with other dNMPs so long as the dT primer can serve as primer. Reverse transcription can be done with reverse transcriptase that has RNase H activity. If one uses an enzyme having RNase H activity, it may be possible to omit a separate RNase H digestion step by carefully choosing the reaction conditions.

In particular, target nucleic acid sequences which may be detected and/or amplified include any naturally occurring procaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

Furthermore, the present invention is very useful in detection of a nucleotide variation. The term "nucleotide variation" used herein refers to a nucleotide polymorphism in a DNA sequence at a particular location among contiguous DNA segments that are otherwise similar in sequence. Such contiguous DNA segments include a gene or any other portion of a chromosome. For example, the nucleotide variation detected in the present invention includes SNP (single nucleotide polymorphism), deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations.

According to a preferred embodiment, the immobilized probe comprises a nucleotide complementary to or corresponding to a nucleotide variation. When the present invention is carried out for detection of a target nucleic acid sequence a nucleotide variation, the target nucleic acid sequence used in step (a) is preferably a pre-amplified nucleic acid sequence.

According to a preferred embodiment, the present invention is carried out using amplification primers for amplifying the target nucleic acid sequence. The present invention performed by cyclic exonucleolytic reactions using DNA polymerases having a 5' to 3' exonuclease together with amplification primers can detect target nucleic acid sequences with amplification of target nucleic acid sequences.

II. Target Detection by ER Using Single-Labeled Probes on Solid Substrate

In another aspect of this invention, there is provided a method for detecting a target nucleic acid sequence from a DNA or a mixture of nucleic acids by an exonucleolytic reaction (ER) on a solid phase, which comprises the steps of:

(a) hybridizing the target nucleic acid sequence with an immobilized probe having a nucleotide sequence complementary to the target nucleic acid sequence and having a single label generating a detectable signal; wherein the immobilized probe is immobilized on a solid substrate through its 3'-end;

(b) contacting the resultant of step (a) to an enzyme having a 5' to 3' exonuclease activity under conditions for cleavage of the immobilized probe; wherein the immobilized probe is digested by the enzyme having the 5' to 3' exonuclease activity to release the single label from the immobilized probe, resulting in decrease in a signal on the solid substrate; and (c) allowing the resultant of step (b) to be kept under the same conditions as step (b) for additional cleavage of an uncleaved immobilized probe in steps (a) and (b), whereby the signal on the solid substrate is further decreased; and (d) detecting the signal decrease on the solid substrate, such that the signal decrease by the cleavage of the immobilized probe is indicative of the presence of the target nucleic acid sequence.

The present invention by ER on the solid substrate is similar to the CER protocol discussed hereinabove, except that the ER protocol follows exonucleolytic reactions instead of cyclic exonucleolytic reactions. Therefore, in the interest of avoiding unnecessary redundancy, the common descriptions between them are not being repeated but they are incorporated into this description of the method as if they were repeated.

In the present invention using a cleavage reaction of probes, where the reaction for hybridization is allowed to be kept at a constant temperature, a cleaved probe is spontaneously released from the target nucleic acid sequence and an uncleaved probe is then hybridized with the target nucleic acid sequence, followed by cleavage and release. Therefore, the present invention by the ER process induces repetition of probe hybridization, cleavage and release, being responsible for amplification of the signal decrease.

In addition, since signal intensities detected on the solid substrate are more decreased with the lapse of time, the ER process of the present invention detects the signal decrease in a time-course manner. The reaction conditions including concentrations and sequences of nucleic acid molecules (target nucleic acid sequences and probes), and type and activity of enzymes used influence on the extent of signal decrease. The measurement of signal decrease patterns provides a variety of useful information (e.g., qualitative and quantitative analysis of target nucleic acid sequences).

In the present invention, the signal decrease may be detected at the end of the reactions or during the reactions, giving rise to more accurate qualitative and quantitative analysis of target nucleic acid sequences. The real-time detection of the signal decrease permits to detect target nucleic acid sequences on the solid substrate in a more convenient and accurate manner.

According to a preferred embodiment, the detection in step (d) is performed at the end of the step (c). Alternatively, the detection in step (d) is performed at each of predetermined time intervals during steps (b) and (c).

Preferably, the detection in step (d) is performed at each of predetermined time intervals during steps (b) and (c).

It is preferable that a cleavage reaction temperature after the hybridization is the same as that for the hybridization. Alternatively, the cleavage reaction temperature after the hybridization may be lower or higher that for the hybridization. For instance, where the hybridization temperature is different from that the optimum temperature for enzyme activity, the cleavage reaction temperature after the hybridization may be adjusted for the optimum enzymatic reaction. The temperature difference between hybridization and cleavage reaction is preferably in a range of ±20° C., more preferably ±10° C., still more preferably ±5° C.

According to a preferred embodiment, the exonucleolytic reaction is an isothermal reaction in which it is carried out for a constant reaction time at a constant reaction temperature after the hybridization.

The reaction time of ER is preferably no more than 2 hr, more preferably no more than 1 hr, still more preferably no more than 30 min.

According to a preferred embodiment, the single label is a fluorescent molecule.

Preferably, the single label on the immobilized probe is located at its 5'-end or at 1-5 nucleotides apart from its 5'-end. Most preferably, the single label on the immobilized probe is located at its 5'-end.

The enzyme having the 5' to 3' exonuclease activity is a non-thermostable exonuclease or a thermostable exonuclease. The non-thermostable enzyme having the 5' to 3' exonuclease activity such as T7 exonuclease and Lamda exonuclease may be used. Preferably, the enzyme having the 5' to 3' exonuclease activity is a thermostable exonuclease, more preferably a template-dependent nucleic acid polymerase having the 5' to 3' exonuclease activity (e.g., E. coli DNA polymerase I, a thermostable DNA polymerase and bacteriophage T7 DNA polymerase), most preferably a thermostable DNA polymerase.

According to a preferred embodiment, the step (a) further comprises an upstream primer or probe to be hybridized with a site downstream of a hybridized site of the immobilized probe.

According to a preferred embodiment, the method is used for a quantitative detection of the target nucleic acid sequence.

Preferably, the target nucleic acid sequence is a pre-amplified nucleic acid sequence.

According to a preferred embodiment, the target nucleic acid sequence comprises at least two types of nucleic acid sequences and the immobilized probe comprises at least two types of probes.

According to a preferred embodiment, the target nucleic acid sequence comprises a nucleotide variation.

III. Kits for Target Detection by CER or ER Using Single-Labeled Probes on Solid Substrate In still another aspect of this invention, there is provided a kit for detecting a target nucleic acid sequence from a DNA or a mixture of nucleic acids by a cyclic exonucleolytic reaction (CER) or an exonucleolytic reaction (ER) on a solid phase, which comprises:

(a) a solid substrate;

(b) an immobilized probe having a nucleotide sequence complementary to the target nucleic acid sequence and having a single label generating a detectable signal; wherein the immobilized probe is immobilized on the solid substrate through its 3'-end; and (c) an enzyme having a 5' to 3' exonuclease activity.

Since the kit of this invention is constructed to perform the detection method of the present invention described above, the common descriptions between them are omitted in order to avoid undue redundancy leading to the complexity of this specification.

The present kits may optionally include the reagents required for performing target amplification PCR reactions (e.g., PCR reactions) such as buffers, DNA polymerase cofactors, and deoxyribonucleotide-5-triphosphates.

Optionally, the kits may also include various polynucleotide molecules, reverse transcriptase, various buffers and reagents, and antibodies that inhibit DNA polymerase activity.

The kits may also include reagents necessary for performing positive and negative control reactions. Optimal amounts of reagents to be used in a given reaction can be readily determined by the skilled artisan having the benefit of the current disclosure. The kits, typically, are adopted to contain the constituents afore-described in separate packaging or compartments.

The features and advantages of the present invention will be summarized as follows:

(a) The present invention enables to detect target nucleic acid sequences on a solid phase using single-labeled systems. Comparing with multiple-labeled systems such as dual labeling, the present invention using single-labeled probes has excellent advantages in light of convenience and cost effectiveness in probe design and preparation.

(b) As discussed hereinabove, the present invention provides that the signal decrease indicative of target nucleic acid sequences is induced depending on both of the hybridization between probes and target sequences and the probe cleavage by enzymatic reactions (5' to 3' exonuclease). Therefore, the target specificity in the present invention is dually determined, permitting to overcome shortcomings of false positive signals by non-specific hybridization associated with conventional probe technologies.

(c) One of the features of the present invention is to detect target nucleic acid sequences by measuring a signal decrease on a solid substrate dependent on release of single label molecules from probes. The conventional methods typically measure or analyze a signal generation (i.e., signal increase) on a solid substrate for determining the presence of target nucleic acid sequences. Therefore, the conventional methods require dual-label systems or the help of additional labeled components (e.g., a labeled ddNTP or an additional labeled probe) in a single label system.

(d) The preferable embodiment of the present invention using cyclic exonucleolytic reactions ensures more effective hybridization between target nucleic acid sequences and probes immobilized on a solid substrate, giving rise to amplification of a signal decrease indicative of target nucleic acid sequences in a more reliable and rapid manner. As addressed in Examples, the embodiment of the present invention using cyclic exonucleolytic reactions shows more rapid signal change (i.e., signal decrease) than that using exonucleolytic reaction.

(e) The present invention measures the final signal at the end of reactions or changes of the signal decrease during reactions. The measurement of changes of the signal decrease during reactions is responsible for more accurate qualitative and quantitative analysis of target nucleic acid sequences.

(f) The present invention allows to measure changes of a signal decrease by exonucleolytic reactions in a time-course for detection of target nucleic acid sequences. The time-course measurement contributes to quantitative detection as well as more reliable detection of target nucleic acid sequences.

(g) The present invention using single-label systems is free from troublesome matters associated with conventional technologies using dual-label systems. According to the conventional technologies using dual-label systems, the positions of reporter and quencher molecules on probes have to be determined in considering the extent of exonuclease action, remaining of reporter molecules on solid substrates after reactions and quenching efficiency between reporter and quencher molecules. However, the present invention permits to avoid these consideration factors.

In addition, the conventional technologies are suffering from the occurrence of background signals due to unstable quenching between reporter and quencher molecules. In contrast, the present invention completely overcomes problems of the background signals.

(h) Where the thermostable 5' to 3' exonuclease is employed, the hybridization step can be performed at high stringency temperatures, ensuring enhanced hybridization specificity between probes and target nucleic acid sequences. Furthermore, the repetition of denaturation and hybridization becomes available by using the thermostable 5' to 3' exonuclease, thereby eliciting a signal decrease in a more effective manner.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Detection of Target Nucleic Acid Sequences by Cyclic Exonucleolytic Reaction Using Single-Labeled Probes Immobilized on the Surface of Solid Substrate We applied a single-labeled probe for the detection of target nucleic acid sequences on solid phase using cyclic exonucleolytic reaction.

For this application, the synthetic oligonucleotide for *Staphylococcus aureus* (SA) gene was used as a template. A probe having a fluorescent reporter molecule (TAMRA) at its 5'-end and poly(T)$_5$ as a linker arm was immobilized on the surface of solid substrate by using an amino group at its 3'-end. As a position marker, a marker probe having a fluorescent molecule (TAMRA) at its 5'-end was immobilized on the surface of solid substrate. Taq polymerase having a 5' to 3' exonuclease activity was used for 5' to 3' exonucleolytic reactions.

The sequences of the synthetic template, the single-labeled probe and the marker used in this Example are:

```
SA_T70
                                                                   (SEQ ID NO: 1)
5'-GGTGTAGGTGGTGGCGGTAACAACGCCGTAAACCGAATGATTGACCACGGAATGAATAATGTTGAATTTA-3'

SA_Con
                                                                   (SEQ ID NO: 2)
5'-[TAMRA]CATTCCGTGGTCAATCATTCGGTTTACGGCGTTGTTACCTTTTT[Amino]-3'
```

Marker

5'-[TAMRA]ATATATATAT[Amino]-3'

(SEQ ID NO: 3)

NSB9 NHS slides (NSBPOSTECH, Korea) were used for fabrication of the probes (SEQ ID NOs: 2 and 3). Each probe dissolved in NSB spotting buffer at the final concentration of 50 μM was printed on the NSB9 NHS slide with Personal-Arrayer™ 16 Microarray Spotter (CapitalBio, China). The probe was spotted side by side in a 2×1 format (duplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 30 min to remove the non-specifically bound probes and rinsed with distilled water. Then the DNA-functionalized slides were dried using slide centrifuge and stored in dark at 4° C. until use.

The cyclic exonucleolytic reaction was conducted on the surface of the DNA-functionalized slide in the final volume of 30 μl containing 10 pmole of synthetic oligonucleotide for SA (SEQ ID NO: 1), 3 μl of 10× reaction buffer (5 mM $MgCl_2$), 50 μM each of dNTPs, and 2 units of Taq DNA polymerase (Solgent, Korea). The whole mixture was applied to a chamber assembled on the surface of NSB glass slide on which the probes were cross-linked. The slide was placed on in situ block in a thermocycler (Genepro B4I, China). Five same slides were prepared for the analysis in each cycle during the cyclic exonucleolytic reaction. The cyclic exonucleolytic reactions were carried out as follows: 2 min initial denaturation at 95° C. and a cycle (0, 5, 10, 30 or 50 cycles) of 95° C. for 20 sec and 55° C. for 20 sec. After the reaction of the corresponding cycle number, the image acquisition for each slide was carried out by the use of Confocal Laser Scanner, Axon GenePix4100A (Molecular Device, USA) with scanning at 10-μm pixel resolution. The fluorescence intensity was analyzed by the use of quantitative microarray analysis software, GenePix software (Molecular Device, USA). The fluorescence intensity was expressed as spot-medians after local background subtractions. Each spot was duplicated for the test of reproducibility. The fluorescence intensity indicates the average value of the duplicated spots.

Figure 2A:
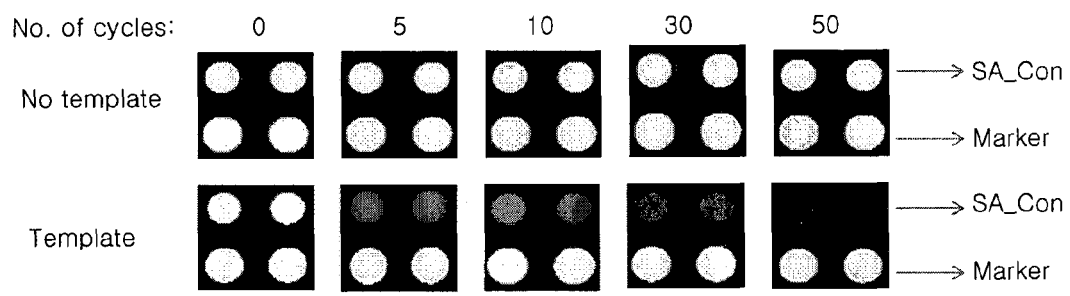

As shown in FIGS. 2A and 2B, when the single-labeled immobilized probe was used in the presence of the template, the fluorescent signal was diminished depending on the number of cycles (0 cycle_RFU: 65,471±1.41; 5 cycles_RFU: 25,375±534.57; 10 cycles_RFU: 16,745±863.38; 30 cycles_RFU: 9,444±247.49; and 50 cycles_RFU: 5,703±608.11). There were no changes in fluorescent signal on various cycle numbers in the absence of the template as a negative control (0 cycle_RFU: 65,471±0.00; 5 cycles_RFU: 65,462±0.00; 10 cycles_RFU: 62,226±9.90; 30 cycles_RFU: 65,454±0.00; and 50 cycles_RFU: 64,699±1,071.91).

Example 2

Detection of Target Nucleic Acid Sequences by Exonucleolytic Reaction Using Single-Labeled Probes Immobilized on the Surface of Solid Substrate We applied a single-labeled probe for the detection of target nucleic acid sequences on solid phase using exonucleolytic reaction.

For this application, the synthetic oligonucleotide for *Staphylococcus aureus* (SA) gene was used as a template. A probe having a fluorescent reporter molecule (TAMRA) at its 5'-end and poly(T)$_5$ as a linker arm was immobilized on the surface of solid substrate by using an amino group at its 3'-end. As a position marker, a marker probe having a fluorescent molecule (TAMRA) at its 5'-end was immobilized on the surface of solid substrate. Taq polymerase having a 5' to 3' exonuclease activity was used for 5' to 3' exonucleolytic reactions.

The sequences of the synthetic template, the single-labeled probe and the marker used in this Example are the same as those in Example 1.

NSB9 NHS slides (NSBPOSTECH, Korea) were used for fabrication of the probes (SEQ ID NOs: 2 and 3). Each probe dissolved in NSB spotting buffer at the final concentration of 50 μM was printed on the NSB9 NHS slide with Personal-Arrayer™ 16 Microarray Spotter (CapitalBio, China). The probe was spotted side by side in a 2×1 format (duplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 30 min to remove the non-specifically bound probes and rinsed with distilled water. Then the DNA-functionalized slides were dried using slide centrifuge and stored in dark at 4° C. until use.

The exonucleolytic reaction was conducted on the surface of the DNA-functionalized slide in the final volume of 30 μl containing 10 pmole of synthetic oligonucleotide for SA (SEQ ID NO: 1), 3 μl of 10× reaction buffer (6 mM $MgCl_2$), 200 μM each of dNTPs, and 1.2 units of Diastar Taq DNA polymerase (Solgent, Korea). The whole mixture was applied to a chamber assembled on the surface of NSB glass slide on which the probes were cross-linked. The slide was placed on in situ block in a thermocycler (Genepro B4I, China). Six same slides were prepared for the predetermined time interval analysis during exonucleolytic reaction. After 2 min initial denaturation at 95° C., the exonucleolytic reactions were carried out in time-dependent manner as follows: 55° C. for 0, 1, 5, 20, 30 or 60 min. After the corresponding predetermined-time incubation, the image acquisition for each slide was carried out by the use of Confocal Laser Scanner, Axon GenePix4100A (Molecular Device, USA) with scanning at 10-μm pixel resolution. The fluorescence intensity was analyzed by the use of quantitative microarray analysis software, GenePix software (Molecular Device, USA). The fluorescence intensity was expressed as spot-medians after local background subtractions. Each spot was duplicated for the test of reproducibility. The fluorescence intensity indicates the average value of the duplicated spots.

Figure 3A:
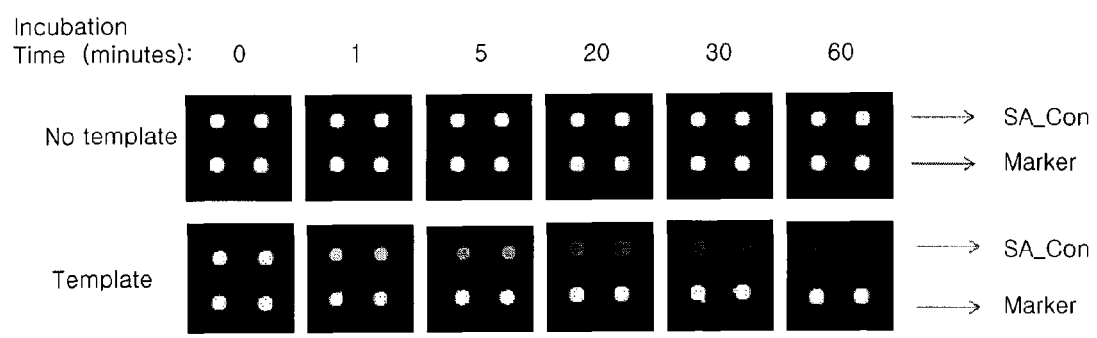

As shown in FIGS. 3A and 3B, when the single-labeled immobilized probe was used in the presence of the template, the fluorescent signal was diminished depending on incubation times (0 min_RFU: 65,449±11.3; 1 min_RFU: 56,576±4,471.0; 5 min_RFU: 29,603±1,547.9; 20 min_RFU: 16,171±206.5; 30 min_RFU: 10,540±47.4; and 60 min_RFU: 5,889±100.4). There were no changes in fluorescent signal on various incubation times in the absence of the template as a negative control (0 min_RFU:

65,464±0.7; 1 min_RFU: 65,433±1.4; 5 min_RFU: 65,444±1.4; 20 min_RFU: 65,443±1.4; 30 min_RFU: 65,426±1.4; and 60 min_RFU: 65,449±0.7).

Example 3

Detection of a Target Nucleic Acid Sequence in Different Amounts by Cyclic Exonucleolytic Reaction We applied a single-labeled probe for the detection of a target nucleic acid sequence in three different amounts on solid phase using cyclic exonucleolytic reaction.

For this application, the synthetic oligonucleotide for *Staphylococcus aureus* (SA) gene was used as a template. A probe having a fluorescent reporter molecule (TAMRA) at its 5'-end and poly(T)$_5$ as a linker arm was immobilized on the surface of solid substrate by using an amino group at its 3'-end. As a position marker, a marker probe having a fluorescent molecule (TAMRA) at its 5'-end was immobilized on the surface of solid substrate by using an amino group at its 3' end. Taq polymerase having a 5' to 3' exonuclease activity was used for 5' to 3' exonucleolytic reactions.

The sequences of the synthetic template, the single-labeled probe and the marker used in this Example are the same as those in Example 1.

NSB9 NHS slides (NSBPOSTECH, Korea) were used for fabrication of the probes (SEQ ID NO: 2 and 3). Each probe dissolved in NSB spotting buffer at the final concentration of 50 µM was printed on the NSB9 NHS slide with Personal-Arrayer™ 16 Microarray Spotter (CapitalBio, China). The probe was spotted side by side in a 2×1 format (duplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 30 min to remove the non-specifically bound probes and rinsed with distilled water. Then the DNA-functionalized slides were dried using slide centrifuge and stored in dark at 4° C. until use.

The cyclic exonucleolytic reaction was conducted on the surface of the DNA-functionalized slide in the final volume of 30 µl containing 10, 1, or 0.1 pmole of synthetic oligonucleotide for SA (SEQ ID NO: 1) as a target nucleic acid sequence, 3 µl of 10× reaction buffer (5 mM MgCl$_2$), 50 µM each of dNTPs, and 2 units of Taq DNA polymerase (Solgent, Korea). The whole mixture was applied to a chamber assembled on the surface of NSB glass slide on which the probes were cross-linked. The slide was placed on in situ block in a thermocycler (Genepro B4I, China). Five slides were used for each examined amount of the target nucleic acid sequence. The cyclic exonucleolytic reactions were carried out as follows: 2 min initial denaturation at 95° C. and a cycle (0, 5, 10, 30 or 50 cycles) of 95° C. for 20 sec and 55° C. for 20 sec. After the reaction of the corresponding cycle number, the image acquisition for each slide was carried out by the use of Confocal Laser Scanner, Axon GenePix4100A (Molecular Device, USA) with scanning at 10-µm pixel resolution. The fluorescence intensity was analyzed by the use of quantitative microarray analysis software, GenePix software (Molecular Device, USA). The fluorescence intensity was expressed as spot-medians after local background subtractions. Each spot was duplicated for the test of reproducibility. The fluorescence intensity indicates the average value of the duplicated spots.

When the single-labeled immobilized probe was used in the presence of the template, the fluorescent signal was diminished depending on the amounts of target nucleic acid sequence.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for detecting a target nucleic acid sequence from a DNA or a mixture of nucleic acids by a cyclic exonucleolytic reaction (CER) with no use of an upstream primer or an upstream probe on a solid phase, which comprises the steps of:
  (a) hybridizing the target nucleic acid sequence with an immobilized probe having a nucleotide sequence complementary to the target nucleic acid sequence and having a single label generating a detectable signal; wherein the immobilized probe is immobilized on a solid substrate through its 3'-end;
  (b) contacting the resultant of step (a) to a thermostable enzyme having a 5' to 3' exonuclease activity under conditions for cleavage of the immobilized probe; wherein the immobilized probe is digested by the thermostable enzyme having the 5' to 3' exonuclease activity to release the single label from the immobilized probe, resulting in decrease in a signal on the solid substrate; wherein the thermostable enzyme having the 5' to 3' exonuclease activity is a template-dependent nucleic acid polymerase having a 5' to 3' exonuclease activity;
  (c) denaturing the resultant of step (b);
  (d) repeating the steps (a)-(c) at least twice to further decrease the signal on the solid substrate with no use of an upstream primer or an upstream probe; and
  (e) detecting the signal decrease on the solid substrate, such that the signal decrease by the cleavage of the immobilized probe is indicative of the presence of the target nucleic acid sequence;
  wherein the upstream primer or the upstream probe is a primer or a probe to be hybridized with a site downstream of a hybridized site of the immobilized probe.

2. The method according to claim 1, wherein the detection is performed at the end of the repetition of step (d).

3. The method according to claim 1, wherein the detection is performed for each cycle of the repetition of step (d).

4. The method according to claim 1, wherein the detection is performed at each of predetermined time intervals during the repetition.

5. The method according to claim 1, wherein the single label is a fluorescent molecule.

6. The method according to claim 1, wherein the single label on the immobilized probe is located at its 5'-end or at 1-5 nucleotides apart from its 5'-end.

7. The method according to claim 1, wherein the step (a) further comprises a reverse primer to produce the target nucleic acid sequence hybridizable with the immobilized probe.

8. The method according to claim 3 or 4, wherein the method is used for a quantitative detection of the target nucleic acid sequence.

9. The method according to claim 1, wherein the target nucleic acid sequence comprises at least two target nucleic acid sequences and the immobilized probe comprises at least two probes.

10. The method according to claim 1, wherein the target nucleic acid sequence comprises a nucleotide variation.

11. A kit for detecting a target nucleic acid sequence from a DNA or a mixture of nucleic acids by a cyclic exonucleolytic reaction (CER) with no use of an upstream primer or an upstream probe on a solid phase for use in the performance of the method of claim 1, which comprises:
  (a) a solid substrate;
  (b) an immobilized probe having a nucleotide sequence complementary to the target nucleic acid sequence and having a single label generating a detectable signal; wherein the immobilized probe is immobilized on the solid substrate through its 3'-end;
  (c) an isolated template-dependent nucleic acid polymerase having a 5' to 3' exonuclease activity; and
  (d) a reverse primer to produce the target nucleic acid sequence hybridizable with the immobilized probe;
  wherein the upstream primer or the upstream probe is a primer or a probe to be hybridized with a site downstream of a hybridized site of the immobilized probe.

12. The kit according to claim 11, wherein the kit is used for a quantitative detection of the target nucleic acid sequence.

13. The kit according to claim 11, wherein the immobilized probe comprises at least two probes.

14. The kit according to claim 11, wherein the immobilized probe comprises a nucleotide complementary to or corresponding to a nucleotide variation.

15. The kit according to claim 11, wherein the template-dependent nucleic acid polymerase having a 5' to 3' exonuclease activity is a thermostable template-dependent nucleic acid polymerase having a 5' to 3' exonuclease activity.

16. The kit according to claim 11, wherein the single label is a fluorescent molecule.

17. The kit according to claim 11, wherein the single label on the immobilized probe is located at its 5'-end or at 1-5 nucleotides apart from its 5'-end.

* * * * *